United States Patent
Bismuth et al.

(10) Patent No.: US 8,855,390 B2
(45) Date of Patent: Oct. 7, 2014

(54) METHOD FOR PROCESSING RADIOLOGICAL IMAGES

(75) Inventors: Vincent Bismuth, Buc (FR); Regis Vaillant, Buc (FR)

(73) Assignee: General Electric Company, Schenectady, NY (US)

(*) Notice: Subject to any disclaimer, the term of this patent is extended or adjusted under 35 U.S.C. 154(b) by 452 days.

(21) Appl. No.: 13/075,897

(22) Filed: Mar. 30, 2011

(65) Prior Publication Data
US 2011/0249790 A1    Oct. 13, 2011

(30) Foreign Application Priority Data

Apr. 2, 2010 (FR) ...................................... 10 52538

(51) Int. Cl.
*G06K 9/00* (2006.01)
*A61B 6/12* (2006.01)
*A61B 6/00* (2006.01)

(52) U.S. Cl.
CPC . *A61B 6/12* (2013.01); *A61B 6/463* (2013.01); *A61B 6/504* (2013.01)
USPC .......................................... 382/130; 382/154

(58) Field of Classification Search
None
See application file for complete search history.

(56) References Cited

U.S. PATENT DOCUMENTS

| 5,453,575 | A  | * | 9/1995 | O'Donnell et al. | 600/463 |
| 5,978,519 | A  |   | 11/1999 | Bollman | |
| 6,560,476 | B1 | * | 5/2003 | Pelletier et al. | 600/410 |
| 6,571,004 | B1 | * | 5/2003 | Florent et al. | 382/128 |
| 6,711,432 | B1 | * | 3/2004 | Krause et al. | 600/427 |
| 2004/0028181 | A1 | * | 2/2004 | Charles, Jr et al. | 378/92 |
| 2004/0111024 | A1 | * | 6/2004 | Zheng et al. | 600/426 |
| 2004/0136491 | A1 | * | 7/2004 | Iatrou et al. | 378/4 |
| 2004/0215071 | A1 | * | 10/2004 | Frank et al. | 600/407 |
| 2005/0203416 | A1 | * | 9/2005 | Angelsen et al. | 600/463 |
| 2007/0116342 | A1 | * | 5/2007 | Zarkh et al. | 382/130 |
| 2010/0312109 | A1 | * | 12/2010 | Satoh | 600/441 |

FOREIGN PATENT DOCUMENTS

| DE | 102008045276 A1 | 3/2010 |
| WO | 02062249 A1 | 8/2002 |
| WO | 03045222 A2 | 6/2003 |

OTHER PUBLICATIONS

Koenig, M. "Automatic cropping of breast regions for registration in MR mammography"; Proceedings vol. 5747 Medical Imaging 2005: Image Processing, J. Michael Fitzpatrick; Joseph M. Reinhardt, Editors, pp. 1563-1570.
Unofficial translation of Search Report and Written Opinion from FR Application No. 1052538 dated Nov. 15, 2010.

* cited by examiner

*Primary Examiner* — Nancy Bitar
(74) *Attorney, Agent, or Firm* — Global Patent Operation; Marc A. Vivenzio

(57) ABSTRACT

A method for processing radiological images is provided. The method includes extracting at least two image portions from at least two radiological images of an area to be treated. The method also includes defining an area in a final image for each extracted image portion. The method further includes laying out the extracted image portions in the final image so that each area of the final image comprises an extracted image portion.

19 Claims, 4 Drawing Sheets

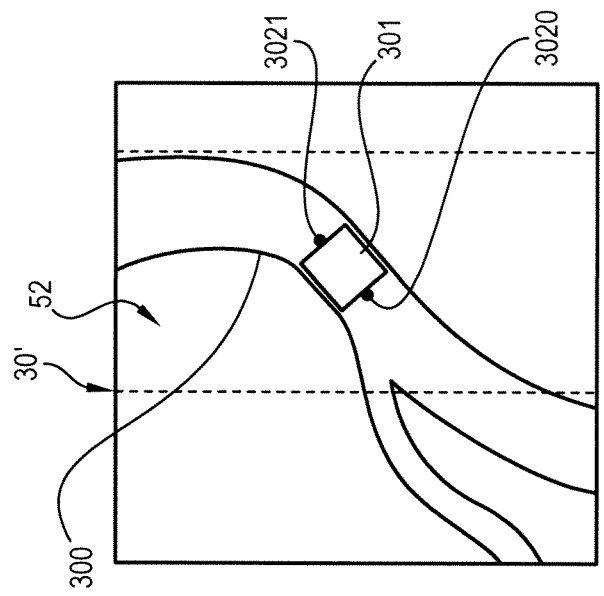
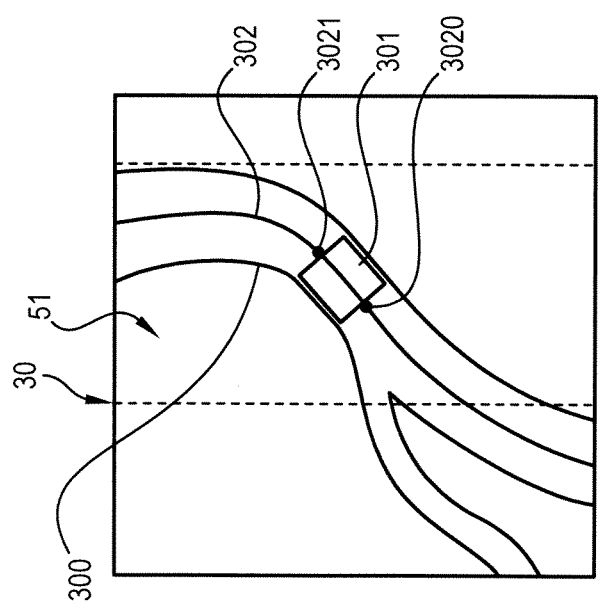

METHOD FOR PROCESSING RADIOLOGICAL IMAGES

BACKGROUND OF THE INVENTION

1. Field of the Invention

The field of the invention relates to the field of medical imaging and more particularly to that of radiology and finds application in the field of vascular radiological interventional imaging.

2. Description of the Prior Art

Vascular interventional radiology includes procedures performed under control of imaging and notably allows atherosclerosis to be treated.

Atherosclerosis is expressed by local shrinkage of the diameter of a vessel and obstruction of the vessel which interferes with circulation of blood flow. The angioplasty operation consists of deploying at the shrinkage area an inflatable balloon so as to widen the diameter of the vessel. An endovascular prosthesis (or stent) may also be implanted in the vessel in order to keep the vessel open.

During the angioplasty operation, the surgeon introduces into the vessel a guide wire with which a catheter supporting the inflatable balloon or the stent may be brought up to the shrinkage area.

The surgeon has to position the stent in a specific location.

The surgeon controls the progress of the operation by viewing a radiological image of the treated area.

The radiological image is an image acquired in real time which allows the surgeon to view the positioning of the different tools used in the area to be treated.

During operation, the surgeon should be able to use two images in parallel, for example an image of a vessel of the area to be treated and an image of the area to be treated with the stent.

Thus, in order to follow the progress of the operation, the surgeon has to mentally superpose both images in order to evaluate the status of the operation in progress or else switch from one image to the other.

SUMMARY OF THE INVENTION

In one embodiment, a method for processing radiological images is provided. The method comprises extracting at least two image portions from at least two radiological images of an area to be treated. The method also comprises defining an area in a final image for each extracted image portion. The method further comprises laying out the extracted image portions in the final image so that each area of the final image comprises an extracted image portion.

In another embodiment, a medical imaging system is provided. The system comprises a source configured to emit a beam of rays, a detector positioned facing the source and configured to detect the rays emitted by the source and a support positioned between the source and the detector. The system also comprises a storage unit and an interface unit. The system further comprises a processing unit configured to: extract at least two image portions from at least two radiological images of an area to be treated; define an area in a final image for each extracted image portion; and lay out the extracted image portions in the final image so that each area of the final image comprises an extracted image portion.

In another embodiment, a computer program is provided.

BRIEF DESCRIPTION OF THE DRAWINGS

Other features and advantages of the invention will further become apparent from the description which follows, which is purely illustrative and non-limiting and should be read with reference to the appended drawings wherein:

FIGS. 3-8 illustrate different images obtained by a method according to one embodiment of the invention.

DETAILED DESCRIPTION OF THE INVENTION

Figure 1:
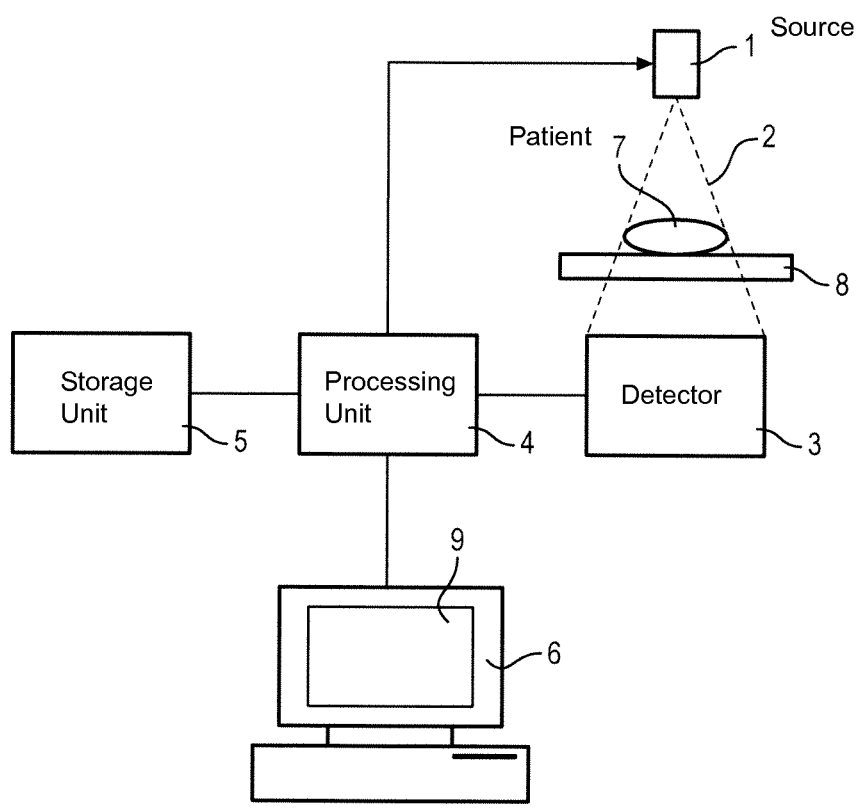
FIG. 1 illustrates a medical imaging system according to one embodiment of the invention.

In FIG. 1, the radiological imaging apparatus comprises a source 1 capable of emitting a beam 2 of X-rays, a detector 3 positioned facing the source 1 and configured for detecting the rays emitted by the source 1, a support 8 positioned between the source 1 and the detector 3, a processing unit 4, a storage unit 5 and an interface unit 6.

The support 8 is intended to receive a patient 7 on which a surgeon has to perform an operation, such as angioplasty, in order to treat atherosclerosis.

The processing unit 4 is configured for controlling the emission of X-rays by the source 1 and the displacement of the source 1 relative to the detector 3.

Further, the processing unit 4 is configured for controlling the readout of an image by the detector 3 and for receiving data acquired by the detector 3.

The processing unit 4 is for example one or more computers, one or more processors, one or more microcontrollers, one or more microcomputers, one or more programmable controllers, one or more specific application integrated circuits, other programmable circuits, or other devices which include a computer such as a work station.

The processing unit 4 is coupled with storage means 5 which may be integrated or separate from the processing unit 4. These means may be formed by a hard disk or any other removable storage means (a CDROM, a diskette, etc.). These storage means 5 may be used for storing an either acquired or processed radiological image of the area to be treated. This may be a ROM/RAM memory of the processing unit 4, a CDROM, a USB key, a memory of a central server. The processing unit 4 may comprise a reader device (not shown), for example a diskette reader or a CDROM reader, for reading the instructions of a method for processing radiological images (which will be described subsequently) from an instruction medium (not shown), such as a diskette or a CDROM. Alternatively, the processing unit 4 executes the instructions of the processing method (which will be described subsequently) stored in microsoftware packages (not shown).

The interface unit 6 comprises a display device 9. The interface unit 6 allows the surgeon to control his procedure.

More specifically, during the operation, the surgeon views the vascular structures of the operated area on the display device 9.

The display device 9 is for example a computer screen, a monitor, a flat screen, a plasma screen or any type of commercially known display device. The display device 9 allows a surgeon to view the vascular structures of the operated area.

Figure 2:
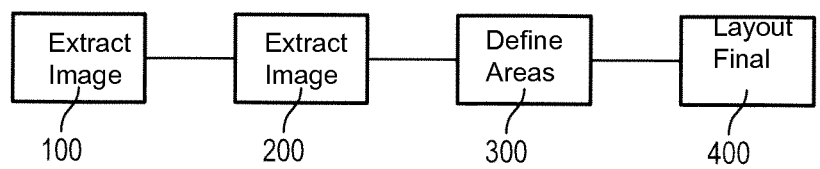
FIG. 2 schematically illustrates the steps of a method according to one embodiment of the invention.

FIG. 2 illustrates the steps of a method according to one embodiment of the invention FIGS. 3 and 4 schematically illustrate a first radiological image of an area to be treated and a second radiological image of an area to be treated, respectively.

Figure 6:
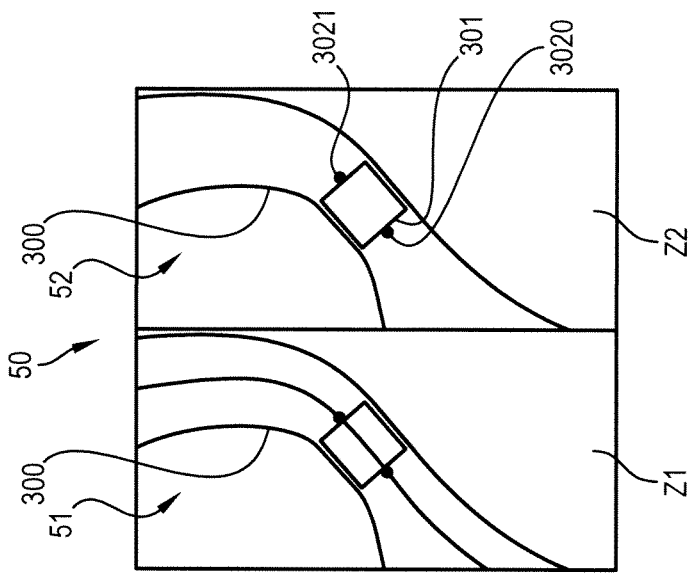
Figure 5:
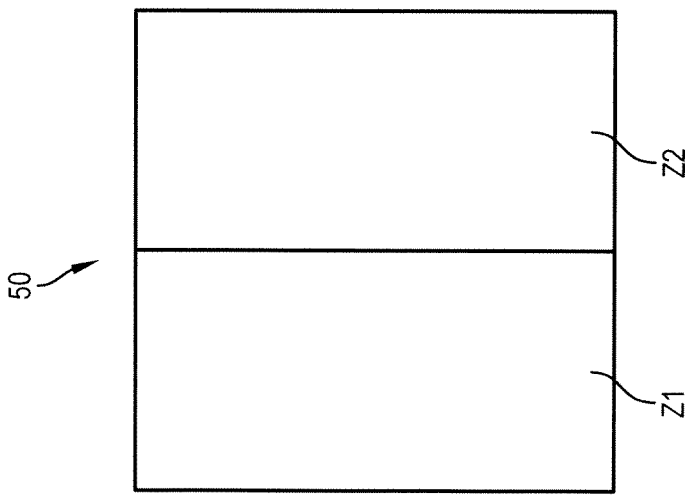

FIGS. 5 and 6 respectively illustrate the final empty image and the final image obtained by a method for processing radiological images.

In the following, a case will be considered when the intention is to display on a single final image 50, two image portions 51, 52 from the first radiological image 30 and from the second radiological image 30' respectively.

The image 30 comprises a vessel 300, a stent 301, a guide wire 302 and markers 3020, 3021. These markers 3020, 3021 are respectively positioned at both ends of the stent 301 and allow the stent 301 to be easily located in the image 30.

It should be noted that the vessel 300 is only viewable when a contrast product is injected into the area to be treated.

The second image 30' differs from the first image 30 in that the guide wire 302 is suppressed (see FIG. 4).

The first image 30 may correspond to an enlargement of an initial radiological image of the area to be treated. Therefore, in this case, the second image 30' corresponds to the first image 30 in which the guide wire is suppressed.

It should be noted that any type of processing of the initial radiological image may be contemplated.

Further, the first and second images may stem from acquisitions at different instants of the area to be treated.

The processing method will allow the first image portion 51 and the second image portion 52 to be laid out on the final image 50. Preferably, the final image is of a size substantially identical with the size of the first image and/or of the second image. Generally, the final image 50 should be able to be displayed on the same type of medium which allows the display of the first image or of the second image.

During the method, in a first step, a first image portion 51 is extracted 100 from the first radiological image 30 and in a second step a second image portion 52 is extracted 200 from the second radiological image 30'. The first image portion 51 is delimited by dashed lines in FIG. 3, the second image portion 52 is delimited by dashed lines in FIG. 4.

The extraction 100, 200 consists of defining an image portion 51, 52 in the relevant image and extracting this image portion.

The dimensions of the extracted image portions 51, 52 may either be identical or not, they depend on the area to be treated but also on the areas which are allocated to them in the final image 50, as is explained below.

In order to lay them out in the final image 50, in a third step 300, two areas Z1, Z2 are defined in the final image, one for each image portion 51, 52.

In this example, the defined areas Z1, Z2 are of identical size and are defined relatively to an axis of symmetry of the square.

Finally, in a fourth step 400, the extracted image portions are laid out on the final image 50.

The final image 50 comprises a number of areas Z1, Z2 equal to the number of extracted portions.

An exemplary embodiment was described above in which the extracted image portions are of a size equal to half of the image from which they stem.

The dimensions of the extracted image portions may be determined automatically or else be a function of the viewed structure on the area to be treated.

Alternatively, the image portions 51, 52 to be extracted may be defined relatively to a preferential axis present in the images and the layout of the extracted image portions in the final image is accomplished parallel to this axis.

A preferential axis is in the example illustrated above, the axis of the vessel or else the axis of the guide wire.

Further, more complex shapes for the extracted image portions may be contemplated.

Figure 8:
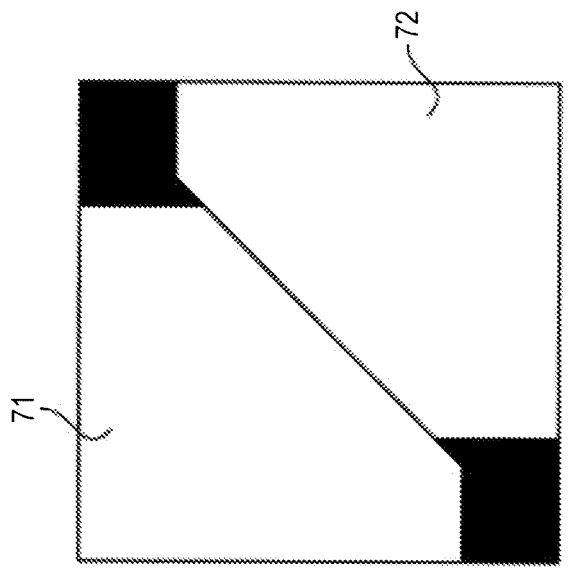
Figure 7:
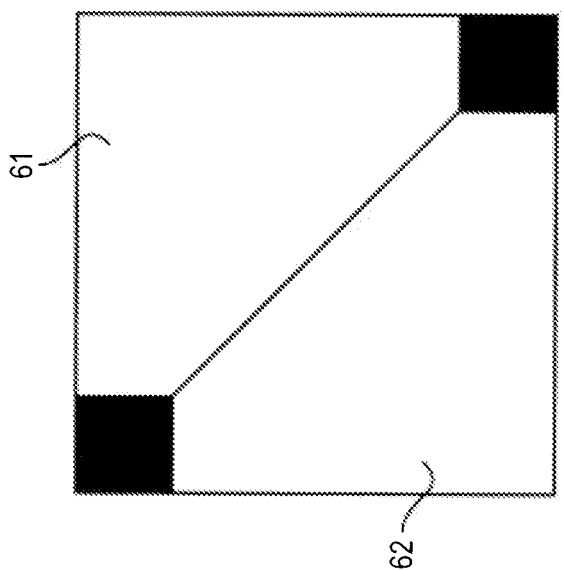

FIGS. 7 and 8 respectively illustrate a final image in which the image portions are laid out on either side of the diagonal of the image but have a surface area of less than half of the surface area of the square.

The method described above may be applied in a processing unit of the medical imaging system described earlier.

Further, the method may be implemented as a computer program comprising machine instructions for applying the method described above.

The embodiments of the invention facilitate the control of progress of processing radiological images. The embodiments allow for both image portions to be laid out on the final image without it being necessary to reduce the size of the images from which they stem. This advantage may be obtained by wisely selecting the image portions.

What is claimed is:

1. A method for processing radiological images of a radiological imaging apparatus, the radiological imaging apparatus including a processing unit, the processing unit configured to execute machine readable instructions for carrying out the method comprising:
   extracting at least two image portions from at least two radiological images of an area to be treated including a first image portion from a first radiological image of the area to be treated and a second image portion from a second radiological image of the area to be treated, the first image portion comprising a vessel, stent and guide wire, and the second image portion comprising the vessel and the stent with the guide wire suppressed;
   defining an area in a final image for each extracted image portion, by at least defining an area in the final image for the first image portion, and defining an area in the final image for the second image portion; and
   laying out the extracted image portions in the final image by at least laying out the first image portion and the second image portion in each defined area in the final image so that the final image comprises the two extracted image portions.

2. The processing method according to claim 1, wherein the radiological images of the area to be treated correspond to an enlargement of an initial radiological image of the area to be treated.

3. The processing method according to claim 1, wherein the final image is a rectangle in which the areas are defined relative to the diagonals of the rectangle, relative to the axes of symmetry of the rectangle, or relative to an axis passing through the center of the rectangle.

4. The processing method according to claim 1, wherein each area is defined by a preferential axis of the image portion to be extracted.

5. The processing method according to claim 1, wherein the final image comprises an area number equal to the number of extracted image portions.

6. The processing method according to claim 1, wherein the at least two radiological images of the area to be treated and the final image are of a substantially identical size.

7. The processing method according to claim 1, wherein the at least two image portions represent a tool or a portion of a tool, wherein the tool is one of an endovascular prosthesis, a guide wire, a catheter, and the combination of several of them.

8. The processing method according to claim 1, wherein the radiological images originate from a sequence of radiological images acquired and recorded beforehand.

9. A medical imaging system comprising:
   a source configured to emit a beam of rays;

a detector positioned facing the source and configured to detect the rays emitted by the source;

a support positioned between the source and the detector;

a storage unit;

an interface unit; and a processing unit configured to:

extract at least two image portions from at least two radiological images of an area to be treated including a first image portion from a first radiological image of the area to be treated and a second image portion from a second radiological image of the area to be treated, the first image portion comprising a vessel, stent and guide wire, and the second image portion comprising the vessel and the stent with the guide wire suppressed;

define an area in a final image for each extracted image portion, by at least defining an area in the final image for the first image portion, and defining an area in the final image for the second image portion; and lay out the extracted image portions in the final image by at least laying out the first image portion and the second image portion in each defined area in the final image so that the final image comprises the two extracted image portions.

10. The method of claim 1, wherein the first and second radiological images are substantially identical.

11. The method of claim 1, comprising:

defining the area in the final image for each extracted image portion by forming areas of identical size defined relative to an axis of symmetry of the defined areas.

12. The method of claim 1, wherein laying out the extracted image portions in the final image comprises defining each extracted image portion in a corresponding area of the final image relative to a preferential axis that is common to each extracted image portion.

13. The method of claim 12, wherein each extracted image portion is laid out on either side of a divider on the final image.

14. The method of claim 1, wherein the final image comprises a number of areas, the number of areas in the final image equal to a number of extracted image portions.

15. The method of claim 1, wherein defining an area in the final image for each extracted image portion comprises defining areas having dimensions of identical size in the final image, one area for each image portion.

16. The method of claim 1, wherein dimensions of the at least two extracted image portions are of a size equal to half of the at least two radiological images.

17. The method of claim 1, wherein each extracted image portion is laid out on either side of a divider on the final image.

18. The method of claim 1, wherein a first image portion is an enlargement of an initial radiological image of the area to be treated.

19. The system of claim 9, wherein the processor is configured to lay out the extracted image portions in the final image by defining each extracted image portion in a corresponding area of the final image relative to a preferential axis that is common to each extracted image portion.

\* \* \* \* \*